United States Patent [19]

Mohrbacher et al.

[11] 4,370,343

[45] Jan. 25, 1983

[54] METHOD FOR CONTROLLING HYPERTENSION

[75] Inventors: Richard Mohrbacher, Maple Glen; Winston Ho, Hatfield; Gene Tutwiler, Churchville, all of Pa.

[73] Assignee: McNeilab, Inc., Fort Washington, Pa.

[21] Appl. No.: 303,753

[22] Filed: Sep. 21, 1981

[51] Int. Cl.³ ............... A61K 31/335; A61K 31/38
[52] U.S. Cl. ............................ 424/275; 424/278
[58] Field of Search ......................... 424/275, 278

[56]  References Cited
U.S. PATENT DOCUMENTS

| | | | |
|---|---|---|---|
| 4,132,719 | 1/1979 | Mohrbacher et al. | 424/278 |
| 4,132,720 | 1/1979 | Mohrbacher et al. | 424/278 |
| 4,196,300 | 4/1980 | Mohrbacher et al. | 424/275 |

OTHER PUBLICATIONS

Frost et al., CA 95:162176a.
Pearce et al., CA 92:52761t.
Tutwiler et al., CA 92:140629m.
McCune et al., CA 92:15328m.
Tutwiler et al., CA 90:97454v.
Tutwiler et al., CA 91:32932a.
Tutwiler et al., CA 91:49305w.
McNeil Lab., CA 92:180975c.

*Primary Examiner*—Jane T. Fan

[57] ABSTRACT

Hypertension is controlled by administration of glycidic or thioglycidic acid derivatives substituted in the α-position with a long chain alkyl or alkenyl or dibromoalkyl radical.

16 Claims, No Drawings

METHOD FOR CONTROLLING HYPERTENSION

This invention relates to a method for controlling hypertension in hypertensive animal subjects by administering a therapeutically effective antihypertensive amount of a glycidic or thioglycidic acid derivative which is substituted in the α-position with a long chain alkyl or alkenyl or dibromoalkyl radical.

The antihypertensive compounds useful in the method of the present invention include those having the following formula:

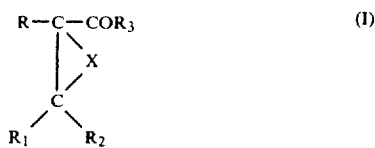

wherein in said formula and in subsequent formulas: R is (a) an alkyl having the formula:

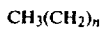

wherein n is an integer from 6 to 21; or (b) an alkenyl having the formula:

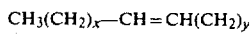

where x and y are each a positive integer, the sum of which (x+y) equals an integer from 8 to 13; or (c) a dibromoalkyl having the formula:

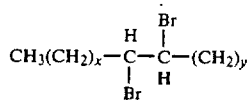

where x and y are as previously defined; $R_3$ is a member selected from the group consisting of OH, O-loweralkyl, $NH_2$, NH-loweralkyl and HN-loweralkyl-OH; X is a member selected from the group consisting of O and S, preferably O; and $R_1$ and $R_2$ are each a member independently selected from the group consisting of hydrogen and loweralkyl. The therapeutically acceptable basic salts of the foregoing acids, i.e., when $R_3$ is OH, are also included within the scope of this invention.

As used herein, the term "loweralkyl" refers to straight or branch chained saturated hydrocarbons having from 1 to 5 carbons, e.g., methyl, ethyl, propyl, isopropyl, sec-butyl, pentyl and the like alkyls.

The preferred compounds, for use in the antihypertensive method of the present invention are those of Formula (I) wherein R is a long chain alkyl, $CH_3$—$(CH_2)_n$, wherein n is an integer from 7 to 19, and wherein $R_1$ and $R_2$ are each hydrogen.

The preferred salt forms of I are additionally capable of forming hydrates and solvates with $H_2O$ and certain organic solvents, respectively. It is naturally intended that the various hydrates and solvates of I be included within the scope of this invention.

DESCRIPTION OF PRIOR ART

Most of the compounds used in the antihypertensive method of the present invention are known compounds appearing in three patents where they are disclosed and shown to have hypoglycemic activity. Thus, U.S. Pat. No. 4,196,300 discloses α-alkyl-substituted glycidate and thioglycidate derivatives having a long chain alkyl of 11–16 carbons, while U.S. Pat. No. 4,132,720 discloses α-alkenyl-substituted glycidate derivatives having a long chain alkenyl of 11–16 carbons, and U.S. Pat. No. 4,132,719 discloses dibromoalkyl-substituted glycidate derivatives having a long chain dibromoalkyl of 11–16 carbons. It has now been unexpectedly discovered that many of the compounds disclosed in said patents, and other compounds closely related thereto have antihypertensive activity.

The compounds useful in the present invention may be made by the processes taught in the above U.S. Pat. Nos. 4,196,300; 4,132,719; and 4,132,720 which are hereby fully incorporated by reference as though fully set forth herein.

The oxy esters of Formula (I), wherein each of said $R_1$ and $R_2$ is hydrogen, are readily obtained from an appropriate α-alkylacrylic acid of Formula (II). Such acids may be obtained according to the synthetic procedure described by Pfeffer et al., J. Org. Chem., 37, 1256 (1972). Conventional esterification of (II), with an appropriate loweralkanol esterifying agent yields the corresponding loweralkyl esters of formula (III). Epoxidation of (III) according to standard oxidation procedures with an appropriate organic percarboxylic acid as the oxidant affords the corresponding loweralkyl α-alkylglycidates of Formula IV. Typical epoxidation peracids include, for example, perbenzoic acid, haloperbenzoic acid, preferably m-chloroperbenzoic acid, monoperphthalic acid, peracetic acid and the like. Among the suitable solvents for the peroxidation reaction are, for example, a halogenated hydrocarbon, e.g., dichloroethane, chloroform and the like, and an ether, e.g., diethyl ether, dioxane and the like.

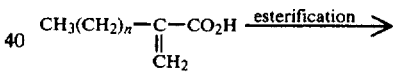

(II)

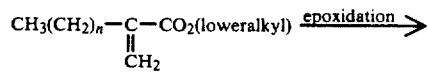

(III)

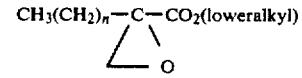

(IV)

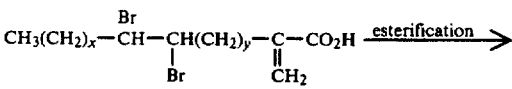

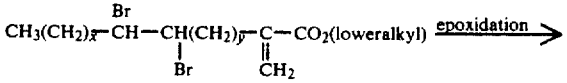

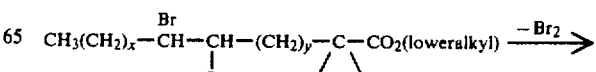

-continued

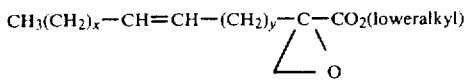

The oxy esters of Formula I, i.e., where X=O, wherein one of said $R_1$ and $R_2$ is loweralkyl, as shown in Formula (VIII), may be prepared from the interaction of an appropriate loweralkyl β-loweralkylacrylate of Formula (V), which has first been treated with a strong base capable of removing an α-hydrogen from said acrylate, with an appropriate alkyl halide of Formula (VI), preferably the bromide or chloride. Typical of the utilizable strong bases are a lithium dialkylamide, e.g., LiN(i-Pr)$_2$, an alkali metal amide, e.g., NaNH$_2$, and the like. The reaction is conducted in a suitable aprotic inert organic solvent under an inert atmosphere, e.g., nitrogen, and preferably at low temperatures of −80° to −30° C. Suitable solvents include the loweralkanes such as hexane, heptane and the like and other solvents whose freezing points are low enough to be suitable for the cooled reaction conditions. A particularly useful solvent system is hexamethylphosphoramide (HMPA) as a cosolvent in tetrahydrofuran (THF). The thus-obtained esters (VII) may then be epoxidized, as previously described, to yield the desired oxy esters of Formula (VIII).

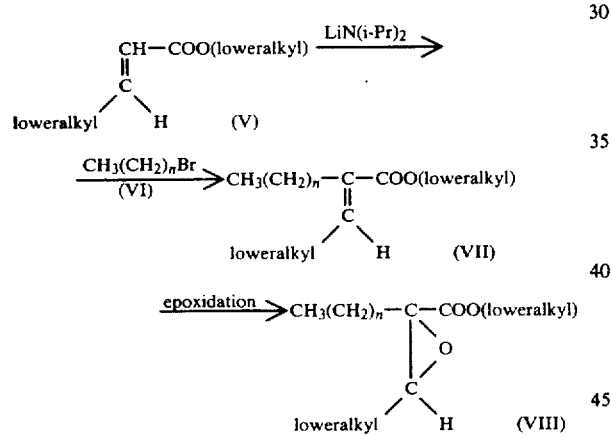

A general method for making all the oxy esters of Formula (I), including those wherein both of said $R_1$ and $R_2$ are loweralkyl, is by the Darzens glycidic ester condensation type of reaction (see Newman in "Organic Reactions", Vol. 5, New York: John Wiley & Sons, Inc., 1949, Chapter 10). An aldol-type condensation of an appropriate aldehyde or ketone with an appropriate α-halo ester produces the glycidic ester. Accordingly, an α-halo ester of Formula (IX), pretreated with a suitable strong base, e.g., an alkali metal alkoxide or amide, capable of removing an α-hydrogen, is reacted with an appropriate aldehyde or ketone of Formula (X) under Darzens reactions conditions to yield the desired oxy esters (XI).

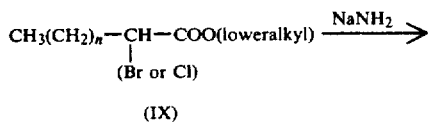

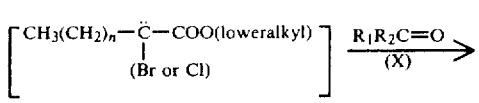

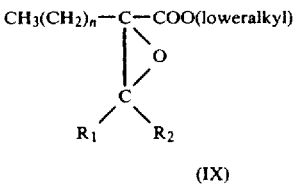

The thio esters of Formula (I), i.e., with X=S, are obtained by transformation of the oxy function in (XI) to a thio function (XI-b) by treating (XI) with thiourea in the presence of a strong mineral acid, preferably sulfuric acid, in a suitable anhydrous organic solvent such as, for example, absolute methanol, ethanol and the like, and then neutralizing the thus-obtained intermediate of Formula (XI-a) with an appropriate base, such as, for example, an alkali metal carbonate or bicarbonate.

The foregoing reactions may be illustrated by the following schematic diagram:

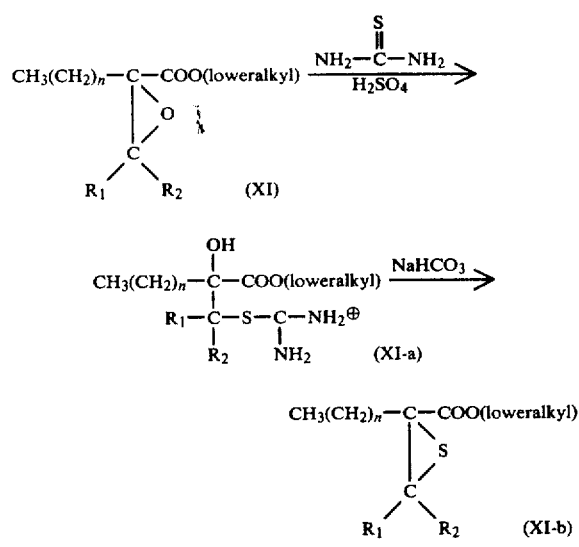

The oxy esters (XI) and the thio esters (XI-b) as shown in combined Formula (XII) wherein X represents O or S, respectively, may then be used as precursors for making other respective oxy and thio derivatives of Formula (I). For example, standard ester-to-acid hydrolysis of (XII) under conventional acidic or alkaline conditions affords the corresponding acids of Formula (XIII). In turn, the acids (XIII) may be reesterified according to standard carboxylic acid-to-ester esterification procedures with an appropriate loweralkanol as the esterifying agent, generally in the presence of a catalytic amount of a strong mineral acid, e.g., HCl, H$_2$SO$_4$ and the like to yield the loweralkyl esters of Formula (XII).

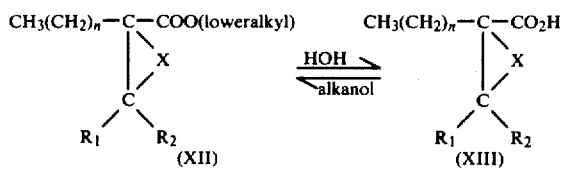

The acids of Formula (XIII) may be converted to the corresponding salt form by treatment with a slight excess of an equivalent amount of an appropriate base, for example, an alkali metal or alkaline earth metal hydroxide, e.g., sodium hydroxide, potassium hydroxide, calcium hydroxide and the like, or with an organic amine base, e.g., mono-, di- and tri-loweralkyl amines such as ethylamine, propylamine, methylethylamine, triethylamine and the like, or other amines such as benzylamine, tromethamine, methylphenylamine, piperidine, pyrrolidine and the like.

The acids (XIII) may also be used as precursors for making the esters, amides and substituted amides of Formula (I). For example, standard esterification procedures with an appropriate loweralkanol as the esterifying agent afford the corresponding loweralkyl esters (XII). The corresponding amides are obtained by standard acid-to-amide procedures, preferably by first transforming the carboxylic function of the acid (XIII) into the corresponding acid chloride form (XIV), for example by treatment of the acid or its alkali metal salt with thionyl chloride or oxalyl chloride in an inert organic solvent suitable for such transformations, e.g., an aromatic hydrocarbon, chloroform and the like, and then reacting the thus-obtained acid chloride with either ammonia or loweralkyl amine in a suitable organic solvent for such ammonolysis reactions, e.g., an aromatic hydrocarbon, acetonitrile and the like, to yield the respective amides of Formulas (XV) and (XVI).

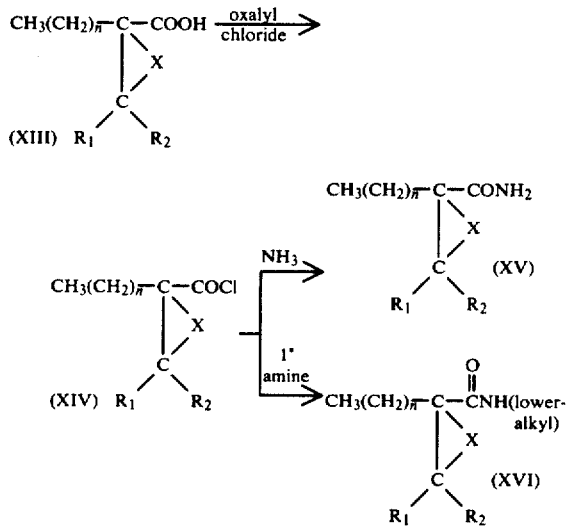

Alternatively, the amides of Formula (I), wherein each of said $R_1$ and $R_2$ is hydrogen, may be prepared from the α-alkylacrylic acids of Formula (II) by similar transformation to the corresponding acid chloride form (XVII) followed by appropriate interaction with ammonia or primary amines to yield the respective -alkyl-acrylic amides (XVIII). Such amides are then epoxidized to the corresponding oxy amides (XIX) which in turn may be converted to the corresponding thio amides (XX) according to the relevant reaction techniques previously described for making the oxy esters and thio esters of Formula (I). The foregoing reactions may be illustrated by the following schematic diagram in which the preparation of unsubstituted amides is exemplified.

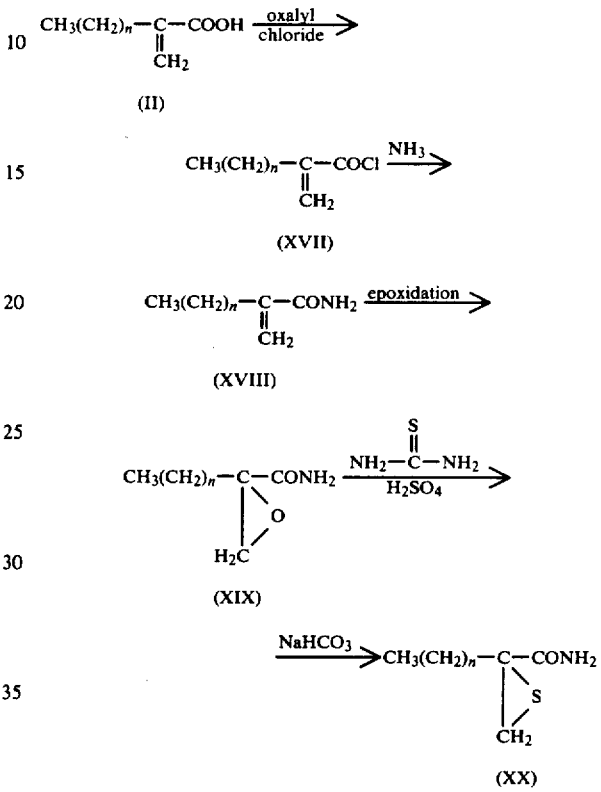

The oxo-amides and thio-amides of Formula (I) may also be conveniently prepared from the acids (XIII) as follows. The acid is first transformed into an appropriate ammonium salt by standard treatment with a tertiary amine, as exemplified by the triethylammonium salt of Formula (XXI). The salt is in turn transformed into a mixed anhydride (XXII) by reaction with an appropriate haloalkylformate, preferably ethyl chloroformate, which anhydride is then reacted with ammonia or an appropriate primary alkylamine in a suitable inert aprotic organic solvent, for example, an ether, e.g., dioxane, tetrahydrofuran, and the like or an aromatic hydrocarbon, e.g., benzene, toluene, xylene and the like to yield the respective amides of Formulas (XV) and (XVI). Reaction of the anhydride with an appropriate alkanolamine in such aprotic solvent yields the compounds of Formula (I) wherein R is NH-loweralkyl-OH.

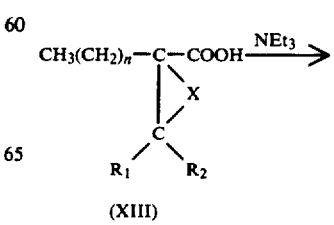

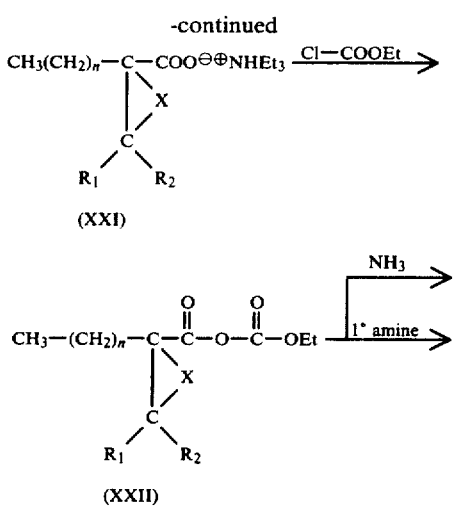

The glycidic or thioglycidic acid derivative compounds of Formula (I) have been found to alleviate hypertension as determined in the following test procedure:

Rodent Antihypertensive Screen

This test evaluates compounds for effects on arterial pressure. In this test, the arterial pressure of adult spontaneously hypertensive rats [SHR] (Charles River) is monitored directly via an aortic cannula. The SHR rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered either orally (p.o.) by gavage or by intraperitoneal (i.p.) injection at doses of 5 to 100 mg/kg. The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control. The results of this test employing at least three rats per dose level for each compound and performed with representative compounds of this invention are shown in Table I.

The results seen in Table I show that α-substituted glycidates and thioglycidates possess beneficial antihypertensive properties.

TABLE I

| | | Antihypertensive Determination Spontaneously Hypertensive (SH) Rat | | |
|---|---|---|---|---|
| Example No. | | Dose mg/kg (p.o.) | Decrease in MAP (mm Hg) | Duration (hrs.) |
| | $CH_3-(CH_2)_n-\overset{\displaystyle C-CO_2CH_3}{\underset{O}{\triangle}}$ | | | |
| VIII | n = 9 | 10 | 32 | 9 |
| VIII | n = 12 | 30 | 43 | 30 |
| VII | n = 13 | 30 | 45 | 9 |
| VIII | n = 15 | 30 | 44 | 8 |
| XXXVII | n = 17 | 100 | 48 | 23 |
| | $R-\overset{\displaystyle C-CO_2CH_3}{\underset{R_1\ \ R_2}{\triangle}}$ | | | |
| XXIX | R = CH$_3$—(CH$_2$)$_7$CH=CH(CH$_2$)$_6$— R$_1$, R$_2$ = H | 10 | 26 | 11 |
| XIX | R = CH$_3$(CH$_2$)$_{13}$— R$_1$, R$_2$ = CH$_3$ | 30 | 29 | 15 |
| | $CH_3(CH_2)_{13}-\overset{\displaystyle C-\overset{O}{\overset{\|}{C}}-R}{\underset{O}{\triangle}}$ | | | |
| | R | | | |
| XI | —ONa | 30 | 30 | 12 |
| VI | —O(CH$_2$)$_3$CH$_3$ | 30 | 41 | 8 |
| XXXII | —OCH$_2$—CHOH—CH$_2$OH | 30 | 39 | 21 |
| XIV | —NH$_2$ | 30 | 32 | 5 |
| XXII | —NHCH$_2$CH$_2$OH | 30 | 23 | 18 |
| IX | $CH_3(CH_2)_{13}\underset{S}{\overset{\displaystyle CO_2CH_3}{\triangle}}$ | 30 | 28 | 7 |

MAP = mean arterial pressure

The compounds of the present invention are useful for treating hypertension (high blood pressure) by administering to subjects in need of treatment, a therapeutically-effective hypertension-reducing amount of a glycidate or thioglycidate of Formula (I) or its pharmaceutically-acceptable salt as active agent.

The active agents may be administered with or without a carrier in the amounts hereinafter set forth. A preferred method of administration is by the use of pharmaceutical compositions in unit dosage form as described below.

The operable ranges for carrying out the treatment is the administration, orally or parenterally, of from about 1 milligram to about 500 milligrams of said glycidate or thioglycidate compound in dosage unit form. While the therapeutic method is most useful for human subjects, it may also be employed for other mammals. Operable amounts are generally within the range of from about 0.5 to 100 mg/kg of body weight.

Pharmaceutical compositions containing the glycidate and thioglycidate compounds of the present invention or base addition salt thereof, as the active ingredient, may be prepared by intimately mixing the compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonfull, tablespoonful and the like, and segregated multiples thereof. A dosage unit generally will contain from about 1 to about 500 mg of the glycidate or thioglycidate compound.

The following examples illustrate the preparation of the glycidate compounds and the novel pharmaceutical compositions suitable in the practice of the invention, but are not to be construed as limiting:

EXAMPLE I

This example illustrates the method described by Pfeffer et al., J. Org. Chem., 37, 1256 (1972), for preparing α-alkylhydracrylic acids of the formula:

$CH_3(CH_2)_n-CH(CH_2OH)-COOH$, wherein n is an integer from 6 to 21. These α-alkylhydracrylic acids are precursors for making the α-alkylacrylic acids of Formula (II).

α-Hydroxymethylpalmitic Acid:

Anhydrous tetrahydrofuran (THF) (825 ml) and 49.5 g (0.49 mole) of diisopropylamine were added to a dry three-neck flask purged with nitrogen and maintained under a nitrogen atmosphere. After cooling the mixture to −20°, 300 ml of n-butyllithium in hexane (1.6 M) (0.49 mole) was added slowly to prevent the temperature from exceeding 0° and then 79.3 ml of anhydrous hexamethylphosphoramide (HMPA) (0.44 mole) was added. A solution of 51.28 g of palmitic acid (0.198 mole) in 400 ml of THF was added dropwise with stirring while maintaining the reaction temperature below 0°. A milky white suspension resulted after the addition of palmitic acid. The reaction mixture was brought to about 40° by using a warm water bath. The suspension changed to a clear solution as the temperature gradually reached 40°. This system was then connected to a formaldehyde generating system. Paraformaldehyde (40 g) was heated to a three-neck flask at 180°-200° to generate formaldehyde and the formaldehyde vapors were carried by a stream of nitrogen over the surface of the stirred solution of α-lithiated lithium palmitate prepared previously. The reaction was terminated after complete depolymerization of paraformaldehyde (2 to 2½ hours). The reaction solution was cooled in an ice bath and neutralized with hydrochloric acid until acidic. The organic layer was separated and was concentrated under reduced pressure on a rotavac to remove most of the THF solvent. The resulting oily residue was dissolved in 2 liters of ether and was washed three times with 10% hydrochloric acid solution and then twice with water. The ether layer was dried over anhydrous $Na_2SO_4$ and the solvents were removed under reduced pressure to give 43.3 g (75%) of crude product, α-hydroxymethylpalmitic acid, which was recrystallized once from acetone to give 39.0 g (69% yield) of the product with m.p. 67°-71°, which was used without further purification in the next synthetic step.

EXAMPLE II

By repeating the procedure of Example I, except that an equivalent amount of an appropriate fatty acid is substituted for the palmitic acid used therein the following respective α-alkylhydracrylic acids are obtained:

| Fatty Acid | Product |
| --- | --- |
| decylic | $CH_3(CH_2)_7CH(CH_2OH)CO_2H$ |
| dodecylic | $CH_3(CH_2)_9CH(CH_2OH)CO_2H$ |
| tridecylic | $CH_3(CH_2)_{10}C(CH_2OH)HCOOH$ |
| tetradecylic | $CH_3(CH_2)_{11}C(CH_2OH)HCOOH$ |
| pentadecylic | $CH_3(CH_2)_{12}C(CH_2OH)HCOOH$ |
| heptadecylic | $CH_3(CH_2)_{14}C(CH_2OH)HCOOH$ |
| Eicosanoic | $CH_3(CH_2)_{17}C-(CH_2OH)HCO_2H$ |
| Oleic | $CH_3(CH_2)_7-CH=CH-(CH_2)_7CO_2H$ |

EXAMPLE III

This example illustrates a method (see Pfeffer et al., ibid.) of preparing the α-alkylacrylic acids of Formula (II) through dehydration of the appropriate α-alkylhydracrylic acid precursor.

A. 2-Tetradecylacrylic Acid:

A 34.25 g sample of α-hydroxymethylpalmitic acid (0.119 mole) and 17 drops of phosphoric acid (85%) were placed in a distillation flask and the mixture heated to 245°-255° C. in an oil bath under vacuum. The product, 2-tetradecylacrylic acid, distilled over at 155°-160° C. at 0.10 mm Hg (24.80 g; 77% yield) and was crystallized from acetone, m.p. 53°-55° C.

B. By repeating the foregoing procedure, except that an equivalent quantity of each of the α-alkylhydracrylic acids obtained in Example II is used as the starting material, the following respective products are obtained:
2-decylacrylic acid
2-undecylacrylic acid
2-dodecylacrylic acid
2-tridecylacrylic acid
2-pentadecylacrylic acid
2-(7-hexadecenyl)-acrylic acid

EXAMPLE IV

A. Methyl 2-Tetradecylacrylate:

14.6 grams of 2-tetradecylacrylic acid (0.052 mole) are combined with 65 ml of absolute methanol and 15 ml of 51% $BF_3$ in methanol in a 200 ml flask equipped with a condenser and drying tube. The system is heated under reflux for six hours (two layers appear when cooled). The mixture is concentrated to ½ volume and the acid is neutralized with saturated $NaHCO_3$ solution to about pH 7. The oily material is extracted with ether, washed with water and dried over anhydrous $MgSO_4$. The ether solvent is removed under reduced pressure. The oily residue of methyl 2-tetradecylacrylate (14.70 g) is not purified further (>95% pure by GC) and used directly in the next step.

B. The foregoing esterification procedure is followed to prepare the loweralkyl α-alkylacrylates of Formula (III). By substituting equivalent quantities of an appropriate α-alkylacrylic acid and an appropriate loweralkanol esterifying agent as starting materials, the following respective products are obtained:
butyl 2-undecylacrylate
methyl 2-dodecylacrylate
methyl 2-tridecylacrylate
ethyl 2-tetradecylacrylate
isopropyl 2-pentadecylacrylate
methyl 2-(cis-7-hexadecenyl)acrylate

EXAMPLE V n-Butyl α-Tetradecyl Acrylate:

4.27 grams (15.9 m mole) of tetradecylacrylic acid is dissolved in 80 ml anhydrous n-butanol in 300 ml one-neck round bottom flask equipped with $CaCl_2$-drying tube, condenser, and magnetic stirrer. 24 ml of 98% $BF_3$ etherate is added and the solution refluxed for 6 hours. The solution is then cooled to room temperature, neutralized with aqueous $NaHCO_3$ to pH 7 and extracted with ether. The ether solution is dried ($MgSO_4$) and evaporated, giving 4.4 g (86% yield) of the product, n-butyl α-tetradecyl acrylate (about 93% pure) which is used without further purification in the next synthetic step.

EXAMPLE VI n-Butyl 2-Tetradecyl Glycidate:

4.2 grams (0.131 mole) of n-butyl α-tetradecyl acrylate (93% pure) is combined with 113 ml dry dichloroethane, 0.0558 g of 3-t-butyl-4-hydroxy-5-methyl phenyl sulfide inhibitor, and 3.5 g (0.0201 mole) of m-chloroperbenzoic acid. The solution is refluxed for 3 hours and then chilled and filtered. The filtrate is successively concentrated to about ½ volume, refiltered, washed with saturated aqueous $K_2CO_3$ and extracted with ether. The ether extract is dried over anhydrous $MgSO_4$ and evaporated in vacuo, and the product recrystallized from absolute methanol with cold filtration to give about 1.8 g of the product, n-butyl 2-tetradecyl glycidate.

EXAMPLE VII

Methyl 2-Tetradecylglycidate:

A mixture of 8.9 g (0.0316 mole) of methyl α-tetradecylacrylate, 10.9 g (0.0632 mole) of m-chloroperbenzoic acid and 0.205 g (0.000572 mole) of 3-t-butyl-4-hydroxy-5-methylphenyl sulfide inhibitor in 300 ml of dry 1,2-dichloroethane is stirred and refluxed for 4 hours. After an additional 18 hours stirring at room temperature, the mixture is filtered and the filtrate concentrated in vacuo to 1/3 volume, cooled and refiltered. Ether is added to the filtrate which is then washed with $K_2CO_3$ solution and then with water. The ether layer is dried over anhydrous magnesium sulfate. After removal of the drying agent the ether solvent is evaporated in vacuo. The oily residue solidifies on cooling to give about 10.6 g of crude product, methyl 2-tetradecylglycidate which is recrystallized from methanol: white crystals, (5.6 g) m.p. 43°–45° C.

EXAMPLE VIII

The epoxidation procedures of Examples VI and VII may be followed in preparing the oxo esters of Formula (IV). For example, by repeating the procedure of Example VII, except that an equivalent amount of an appropriate loweralkyl 2-alkylacrylate is employed as the material to be epoxidized, the following products are obtained:
methyl decylglycidate
butyl 2-undecylglycidate
methyl 2-dodecylglycidate, m.p. 38°–42° C.
methyl 2-tridecylglycidate, m.p. 38°–39° C.
methyl 2-pentadecylglycidate
ethyl 2-tetradecylglycidate
isopropyl 2-pentadecylglycidate
methyl 2-(7,8-dibromohexadecyl)-glycidate
methyl 2-(cis,-7,8-hexadecenyl)-glycidate

EXAMPLE IX

Methyl 2-Tetradecylthioglycidate:

1.27 grams (0.0167 mole of thiourea and 5.00 ml of 95–98% $H_2SO_4$ are placed in a one-liter, three-neck, round-bottom flask equipped with a condenser, magnetic stirrer and addition funnel along with 400 ml of absolute methanol. Then 5.00 g (0.0167 mole) of methyl 2-tetradecylglycidate dissolved in 50 ml of absolute methanol is added and the mixture stirred at room temperature for 3 hours. 400 ml more of absolute methanol is added and the mixture is neutralized by addition of $NaHCO_3$ (1.7 g) with stirring. When the pH rises above 7 an oily material is seen to come out of the solution, and at this point, the neutralization is considered complete. The solvent is removed in vacuo and the residue partitioned between water and ether. The ethereal layer is washed twice with $H_2O$ and once with saturated NaCl solution, dried over anhydrous $Na_2SO_4$ and concentrated in vacuo to yield about 5.77 g of a light tan solid. Column chromatography is employed to isolate the pure material, methyl 2-tetradecylthioglycidate.

EXAMPLE X

By following the procedure of Example IX, the transformation of the oxo function in Formula (IV) compounds to the thio function in Formula (XI) compounds is accomplished. For example, by substituting an equivalent amount of each of the oxo esters obtained in Example VIII for the methyl 2-tetradecylglycidate used in Example IX, the following thio glycidates of Formula (XI) are obtained:
butyl 2-undecylthioglycidate
methyl 2-dodecylthioglycidate
methyl 2-tridecylthioglycidate
ethyl 2-tetradecylthioglycidate
isopropyl 2-pentadecylthioglycidate

EXAMPLE XI

A. 2-Tetradecylglycidic Acid:

3.6 grams (12.2 mmole) of methyl 2-tetradecylglycidate is dissolved in minimal absolute ethanol (about 40 ml) and set aside. 10.8 ml of absolute ethanol is placed in a 100 ml three-neck, round-bottom flask equipped with magnetic stirrer, $CaCl_2$ drying tube, thermometer and addition funnel. The ethanol is chilled in an ice bath and 0.3 g of sodium metal is added. When formation of sodium ethoxide is completed, the ethanol solution of methyl 2-tetradecylglycidate is added dropwise. After addition is completed and stirred for 15 minutes, 0.24 g of water is added and the mixture is stirred (25° C.) overnight (about 15 hours). The resulting suspension is filtered (sintered funnel) and the precipitate washed with ether, dried and then combined with 75 ml 1 N HCl and stirred for 4 hours. The suspension is extracted into ether. The ether extract is dried over anhydrous $Na_2SO_4$ and evaporated in vacuo, giving quantitative conversion to the acid. Recrystallization from acetone gives about 2.5 g (74% yield) of the product, 2-tetradecylglycidic acid, m.p. 77°–79°C.

B. The ester-to-acid hydrolysis procedure of Example XI-A illustrates a method of making the 2-alkylglycidic acids of formula (XIII). For example, by utilizing therein an equivalent amount of each oxo esters obtained from Example VIII, the corresponding oxo acids of Formula (XIII) are respectively obtained.

EXAMPLE XII

A. 2-Tetradecylthioglycidic Acid:

A solution of 3.15 g (0.01 mole) of methyl 2-tetradecylthioglycidate in 50 ml of absolute ethanol is added dropwise to a cooled (0°–5° C.) solution of sodium ethoxide (0.25 g sodium in 12 ml absolute ethanol). The mixture is stirred for 15 minutes while maintaining the temperature below 20° C. and 0.19 g of water is added. Stirring is continued overnight (about 15 hours) at room temperature. The resulting suspension is filtered and the precipitate washed with ether, dried and then stirred for several hours in dilute HCl. The acidic suspension is extracted with ether and the ether layer dried ($Na_2SO_4$) and evaporated in vacuo giving the product, 2-tetradecylthioglycidic acid, in good yield.

B. The ester-to-acid hydrolysis procedure of Example XII-A illustrates a method for making the 2-alkylthioglycidic acid of formula (XIII). For example, by utilizing therein an equivalent amount of each thio ester obtained from Example X, the corresponding thio acids of Formula (XIII) are respectively obtained.

EXAMPLE XIII

A. 2-Tetradecylacrylamide:

5.4 grams (0.02 mole) of 2-tetradecylacrylic acid is dissolved in 200 ml benzene and combined with 10.7 ml oxalyl chloride and stirred overnight (bubbling noted). The mixture is evaporated and the residue dissolved in benzene. The benzene solution is evaporated to dryness. This dissolution in and evaporation of benzene is repeated three times to ensure removal of unreacted oxalyl chloride and other noxious gaseous by-products. The residue containing 2-tetradecylacrylic acid chloride is combined with 100 ml benzene and 80 ml of 4.7% ammonia in acetonitrile. The mixture is stirred overnight and then filtered. Filtration gives about 4.5 g of solid material containing some $NH_4Cl$ as a by-product. The filtrate is washed with water, dried ($Na_2SO_4$) and evaporated to give about 1.6 g of oily residue (residue A). The 4.5 grams of filtered solid material is mixed with 100 ml of diethylether/chloroform (1:1) and the resultant solution is washed with water. The organic phase is then dried ($Na_2SO_4$) and evaporated to give about 3.1 g of oily residue (residue B). the two oily residues (A and B), containing the product, 2-tetradecylacrylamide, are combined and used in the next synthetic step (see Example XIV-A) without further purification.

B. The foregoing acid-to-acid chloride-to-acid amide synthesis illustrates an amidation procedure which can be used to prepare the α-alkylacrylic amides of Formula (XIX). By repeating such procedure, except that an equivalent quantity of each α-alkylacrylic acid obtained from Example III-B is substituted for the 2-tetradecylacrylic acid utilized in Example XIII-A, there are obtained, as respective products, the corresponding 2-alkylacrylamides.

EXAMPLE XIV

A. 2-Tetradecylglycidamide:

4.0 grams of 2-methylene hexadecanoamide is combined with 145 ml dry 1,3-dichloroethane, 0.083 g of 3-t-butyl-4-hydroxy-5-methylphenyl sulfide inhibitor and 4.4 g of m-chloro perbenzoic acid (85%). The mixture is heated to reflux for 3 hours with stirring. The mixture is then cooled to room temperature and concentrated to about ⅓ volume. The decreased volume is filtered and the filtrate washed with saturated aqueous $K_2CO_3$ and extracted with chloroform. The chloroform extract is dried ($MgSO_4$) evaporated and the crude product recrystallized from absolute methanol to give about 1.1 g of 2-tetradecylglycidamide, m.p. 104°–106° C.

B. The epoxidation procedure of Example XIV-A is repeated, except that an equivalent quantity of each 2-alkylacrylamide obtained in Example XIII-B is substituted as the starting material to be epoxidized, to yield the following respective oxyamides of Formula (XX):
2-undecylglycidamide
3-dodecylglycidamide
2-tridecylglycidamide
2-pentadecylglycidamide

EXAMPLE XV

The procedure described in Example X for the transformation of oxo esters to thio esters is followed to also transform the oxo amides of Formula (XX) to thio amides of Formula (XXI). Accordingly, substitution of an equivalent amount of each of the oxo amides obtained in Examples XIV-A and B for the methyl 2-tetradecylglycidate used in Example IX affords the corresponding 2-alkylthioglycidamides of Formula (XXI) as respective products.

EXAMPLE XVI

A. Methyl 2-Tetradecylcrotonate:

To a solution of distilled di-isopropylamine (5.06 g; 0.05 mole) in 50 ml anhydrous THF maintained at −78°

C. is added dropwise 36 ml of n-butyllithium in hexane (1.39 M; 0.05 mole) under nitrogen atmosphere, followed by dropwise addition of anhydrous HMPA (9.86 g; 0.055 mole). The mixture is maintained at −78° C. for about ½ hour and then methyl crotonate (5 g; 0.05 mole) is added dropwise. Ten minutes following complete addition of the methyl crotonate, 15.3 g of myristyl bromide (0.055 mole) is added. The system is then allowed to warm to ≦ −30° C. and is maintained at this temperature for about 1 hour with stirring. The system is then allowed to reach ambient temperature with continued stirring overnight (about 15 hours). The system is acidified to pH 5 with 1 N HCl and then extracted with ether. The ether extract is washed successively with water and saturated brine, then dried over anhydrous $Na_2SO_4$ and evaporated in vacuo. The crude oily product is purified by column chromatography (silica gel):

| Fraction No. | Eluting solvent | Volume of solvent |
| --- | --- | --- |
| 1–5 | 100% pet ether | 1000 ml |
| 6–13 | 10% benzene in pet ether | 1000 ml |
| 14–22 | 25% benzene in pet ether | 1000 ml |

Fractions Nos. 20–22 are combined and the oily product, methyl 2-tetradecylcrotonate, is obtained in 98.4% purity by standard isolation techniques.

B. The procedure of Example XVI-A illustrates a method of preparing the unsaturated esters of Formula (VII). By following such procedure, except that an equivalent amount of the appropriate precursors are utilized, the following products are obtained:

$$CH_3(CH_2)_n\text{---}\underset{\underset{\underset{loweralkyl}{}\diagup\phantom{XXX}\diagdown\underset{}{H}}{C}}{\overset{\|}{C}}\text{---}COO(l.a.) \qquad (VII)$$

| n | loweralkyl | —COO(l.a.) |
| --- | --- | --- |
| 10 | Me | —COOEt |
| 11 | n-Pr | —COOMe |
| 13 | n-Bu | —COOPr |
| 14 | Me | —COOMe |

EXAMPLE XVII

A. Methyl 2-tetradecyl-3-methylglycidate:

1.09 grams (3.7 mmole) of methyl 2-tetradecylcrotonate is combined with 62 ml dry 1,2-dichloroethane, 0.037 g (0.103 mmole) of 3-t-butyl-4-hydroxy-5-methylphenyl sulfide inhibitor and 1.3 g (7.4 mmole) of m-chloroperbenzoic acid. The mixture is refluxed for 4 hours. After the additional 18 hours stirring at room temperature, the mixture is filtered and the filtrate concentrated in vacuo to ½ volume, cooled and refiltered. Ether is added to the filtrate which is then extracted with $K_2CO_3$ solution and then with water. The ether layer is dried over anhydrous $MgSO_4$. After removal of the drying agent, the ether solvent is evaporated in vacuo. The oily residue is purified by column chromatography (silica gel):

| Fraction No. | Eluting solvent | Volume of solvent |
| --- | --- | --- |
| 1 | 100% pet ether | 50 ml |
| 2–10 | 10% $Et_2O$ in pet ether | 200 ml |
| 11 | 25% $Et_2O$ in pet ether | 100 ml |

Fractions 7–9 are combined and the product, methyl 2-tetra-decyl-3-methylglycidate, is obtained by standard isolation techniques.

B. The epoxidation procedure of Example XVII-A is repeated, except that an equivalent amount of each of the unsaturated esters obtained in Example XVI-B are utilized as the starting material to be epoxidized to yield, as respective products, the corresponding 3-substituted oxo esters of Formula (VIII).

C. By following the procedure of Example IX, except that an equivalent amount of the 3-substituted oxoesters obtained from Examples XVII-A and B are utilized as the starting material, transformation of the oxo function to a thio function is accomplished to give the corresponding 3-substituted thio esters of Formula (XI-B).

D. The ester-to-acid hydrolysis procedures of Examples XI and XII are followed to prepare the corresponding 3-substituted oxo and thio acids of Formula (XIII) by starting with an equivalent amount of each of the 3-substituted esters obtained heretofore in this example.

EXAMPLE XVIII

A. N-Ethyl-2-tetradecylthioglycidamide:

To a stirred solution of 0.3 g (0.001 mole) of 2-tetradecylthioglycidic acid in 10 ml of anhydrous tetrahydrofuran (THF) at 0° C. (ice water bath) is added 1.01 g (0.001 mole) of triethylamine in a small amount of THF. The mixture is stirred at 0° C. for about 30 minutes. To the thus-formed triethylammonium 2-tetradecylthioglycidate is added 0.108 g (0.001 mole) of ethyl chloroformate in a small amount of THF and the mixture is stirred at about 0° C. (ice water bath) for about 3 hours to prepare the corresponding mixed anhydride (a ppt. of $Et_3NHCl$ is observed). A stoichiometric excess of ethylamine in THF is then added and the mixture stirred at room temperature for 16 hours. The THF solvent is concentrated to approximately ¼ volume, water is added and the mixture extracted with ether. After drying the ether extract ($Na_2SO_4$), the solvent is removed in vacuo giving the desired product, N-ethyl-2-tetradecylthioglycidamide, in good yield.

B. By repeating the acid-to-amide procedure of Example XVI-A, except that an equivalent amount of an appropriate 2-alkylglycidic acid or 2-alkylthioglycidic acid and an appropriate primary amine are employed as precursors, the following respective products are obtained:

N-methyl-2-octylglycidamide
N-methyl-2-tetradecylglycidamide
N-methyl-N-ethyl-2-tridecylglycidamide
N-(n-butyl)-2-tridecylglycidamide
N-ethyl-2-tetradecyl-3-methylglycidamide

EXAMPLE XIX

This example demonstrates a Darzens glycidic ester synthesis for making the oxo esters of Formula (I).

A. Methyl 2-tetradecyl-3,3-dimethylglycidate:

To a solution of 2.068 g of methyl bromopalmitate (0.0059 mole) in 0.343 g of acetone at 10°–15° C. with stirring is slowly added 5.57 ml of potassium t-butoxide solution (prepared from 0.58 g potassium and 16.5 ml t-butanol). The reaction mixture is stirred at room temperature for about 1 hour. Ether is added and the ether layer is separated and washed successively with dilute HCl, water and saturated brine. The ether layer is then dried over anhydrous MgSO₄ and the solvent evaporated off leaving an oily residue (about 1.84 g crude) which is purified by chromatography over silica gel in pet-ether (wet-packed; using 5% ether in pet-ether as eluting solution) to give the product, methyl 2-tetradecyl-3,3-dimethyl-glycidate in about 38% yield; m.p. 39°-40° C.

B. By following the procedure of Example XIX-A, except that an equivalent quantity of an appropriate aldehyde or ketone is used in place of the acetone used therein, the following respective products are obtained:
methyl 2-tetradecylglycidate
methyl 2-tetradecyl-3-methylglycidate
methyl 2-tetradecyl-3-methyl-3-ethylglycidate
methyl 2-tetradecyl-3,3-diethylglycidate

EXAMPLE XX

Transformation of the oxy function in each of the oxy esters obtained in Example XIX to a thio function according to the relevant procedures previously described yields the following thioglycidates of Formula (I):
methyl 2-tetradecyl-3,3-dimethylthioglycidate
methyl 2-tetradecylthioglycidate
methyl 2-tetradecyl-3-methylthioglycidate
methyl 2-tetradecyl-3-methyl-3-ethylthioglycidate
methyl 2-tetradecyl-3,3-diethylthioglycidate

EXAMPLE XXI

A. Hydrolysis of the ester function in each appropriate oxy ester obtained in Example XIX and in each appropriate thio ester obtained in Example XX according to the relevant procedures previously described affords the following corresponding acids of Formula (I):
2-tetradecyl-3-methylglycidic acid
2-tetradecylthioglycidic acid
2-tetradecyl-3-methylglycidic acid B. By following the applicable acid-to-amide procedures described in Examples XIV and XV, each of the foregoing acids are converted into the corresponding amides of Formula (I).

EXAMPLE XXII

N-(2-hydroxyethyl)-2-tetradecylglycidamide:

To a solution of 0.2 g of 2-tetradecylglycidic acid (0.0007 mole) in 10 ml of anhydrous THF at 0° C. (ice water bath) with stirring is added 0.070 g of triethylamine (0.0007 mole) in a small amount of THF. The solution is stirred at 0° for 30 minutes and 76 mg of ethyl chloroformate (0.0007 mole) in a small amount of THF is added. The mixture is stirred at about 0° C. (ice water bath) for 3 hours (ppt. of Et₃NHCl observed). At the end of 3 hours, 0.042 g (0.0007 mole) of ethanolamine in THF is added. The mixture is stirred at room temperature for 16 hours. The THF solvent is concentrated to about ⅓ its volume, water is added and the mixture extracted with ether. The ether extract is dried over Na₂SO₄ and the ether solvent removed to give a white solid of N-(2-hydroxyethyl)-2-tetradecylglycidamide which, upon recrystallization from acetone has a m.p. of 80°-82° C.

EXAMPLE XXIII

By repeating the procedure of Example XXII, except that an equivalent quantity of an appropriate 2-alkylglycidic acid or 2-alkylthioglycidic acid and an appropriate alkanolamine are employed as precursors, the following respective products are obtained:
N-(2-hydroxyethyl)-2-tridecylglycidamide
N-(2-hydroxyethyl)-2-pentadecylglycidamide
N-(3-hydroxypropyl)-2-tetradecylglycidamide
N-(2-hydroxyethyl)-2-dodecylthioglycidamide
N-(2-hydroxyethyl)-2-tetradecylthioglycidamide
N-(3-hydroxypropyl)-2-pentadecylglycidamide

EXAMPLE XXIV

α-Hydroxymethyloleic Acid:

Anhydrous tetrahydrofuran (600 ml) and 24.5 g (0.24 mole) of diisopropylamine is added to a dry, three-neck flask purged with nitrogen and maintained under a nitrogen atmosphere. After cooling the mixture to −20° C., 94 ml of n-butyllithium in hexane (2.6 M) (0.24 mole) was added slowly to prevent the temperature from exceeding 0° C. and then 40 ml of anhydrous hexamethylphosphoramide (HMPA) (0.22 mole) is added. To the thus prepared in situ solution of lithium diisopropylamide (LDA), a solution of 28.2 g of oleic acid (0.1 mole) in 30 ml of tetrahydrofuran (THF) dropwise with stirring while maintaining the reaction temperature below 0° C. A milky white suspension results after the addition of oleic acid. The reaction mixture is brought to about 40° C. by using a warm water bath. The suspension changes to a clear solution as the temperature gradually reaches 40° C. This system is then connected to a formaldehyde generating system. Paraformaldehyde (20 g) is heated in a three-neck flask at 180°-200° C. to generate formaldehyde and the formaldehyde vapors are carried by a stream of nitrogen over the surface of the stirred solution of α-lithiated lithium oleate prepared previously. After complete depolymerization of paraformaldehyde, the reaction solution is cooled in an ice bath and acidified with hydrochloric acid until acidic. The organic layer is separated and is concentrated under reduced pressure on a rotavac to remove most of the THF solvent. The resulting oily residue is dissolved in about 500 ml of ether, washed with 10% hydrochloric acid solution and then with water. The ether layer is dried over Na₂SO₄ and the solvent is removed under reduced pressure to give 23.0 g of crude product, (80% yield), α-hydroxymethyloleic acid, which is used without purification in the next synthetic step.

EXAMPLE XXV 2-(7,8-Hexadecenyl)acrylic Acid:

A 9.0 g sample of α-hydroxymethyloleic acid (0.028 mole) and 4 drops of phosphoric acid (85%) are placed in a distillation flask and the mixture is heated to 270°-280° C. in an oil bath under vacuum. The product, 2-cis-7,8-hexadecenylacrylic acid, is distilled over at 190°-195° C. at 0.05 mm Hg (4.2 g; 53% yield).

EXAMPLE XXVI 2-(7,8-Dibromohexadecyl)-acrylic Acid:

To a solution of 3.5 g (0.0119 mole) of 2-cis-7,8-hexadecenylacrylic acid in 100 ml of carbon tetrachloride at 0° C. (ice water bath) is added slowly 1.90 g of liquid bromine (0.0119 mole). The solvent is removed under reduced pressure, the residue is taken up in ether, washed with water and dried over Na$_2$SO$_4$. Removal of the ether solvent gives 5.1 g of oily crude product, 2-(7,8-dibromohexadecyl)-acrylic acid.

EXAMPLE XXVII

Methyl 2-(7,8-Dibromohexadecyl)-acrylate:

The crude dibromo acid, 2-(7,8-dibromohexadecyl)-acrylic acid is dissolved in 50 ml of methanol and 5 ml of boron trifluoride methanol solution is added. The solution is heated under reflux for 6 hours. The solution is concentrated to ½ volume and the acid is neutralized with saturated NaHCO$_3$ solution to about pH 7. The oily material is extracted with ether, washed with water and dried over Na$_2$SO$_4$. The ether solvent is removed under reduced pressure to give 4.80 g of crude product, methyl 2-(7,8-dibromohexadecyl)-acrylate.

EXAMPLE XXVIII

Methyl 2-(7,8-Dibromohexadecyl)-glycidate:

A mixture of 3.80 g (0.0081 mole) of methyl 2-(7,8-dibromohexadecyl)-acrylate, 2.76 g (0.016 mole) of m-chloroperbenzoic acid and 50 mg of 3-t-butyl-4-hydroxy-5-methylphenyl sulfide in 50 ml of dry 1,2-dichloroethane is stirred and refluxed for 4 hours. The mixture is cooled, filtered, and the filtrate concentrated, and about 100 ml of petroleum ether is added. The insoluble solid is filtered again and discarded. The filtrate is concentrated to dryness to give 4.2 g of oily residue. It is purified by dry column chromatography using 400 g of silica gel and eluting the column with 5% ether in petroleum ether. There is obtained 3.03 g of pure oily product, methyl 2-(7,8-dibromohexadecyl)-glycidate.

EXAMPLE XXIX

Methyl 2-(7-Hexadecenyl)-glycidate:

To a stirred mixture of 3.32 g (0.069 mole) of methyl 2-(7,8-dibromohexadecyl))-glycidate and 9.0 g of zinc dust in 150 ml of DMF is added 1.50 g of anhydrous potassium carbonate and a few crystals of iodine. The mixture is maintained at 50° C. for 3.5 hours. The reaction is monitored by thin layer chromatography (TLC). The occasional addition of iodine crystals is employed to speed up the reaction. Ether is added and the zinc dust then removed by filtration. The filtrate is washed with water and dried over Na$_2$SO$_4$. On removal of the ether solvent there is obtained about 2.3 g of oily product which is purified by dry column chromatography using 100 g of silica gel and eluting it with 5% ether in petroleum ether. About 1.30 g of pure oily methyl 2-(cis-7,8-hexadecenyl)-glycidate is obtained.

EXAMPLE XXX 2-(7-Hexadecenyl)-glycidic Acid:

To 3.24 g (0.01 mole) of methyl 2-(cis-7,8-hexadecenyl)-glycidate at room temperature is added 10 ml methanol solution containing 0.857 g of anhydrous barium hydroxide. The mixture is stirred at room temperature for 48 hours. The methanol is removed under reduced pressure and the oily residue is triturated with ether until solidification of the residue. The solid is collected on filter, washed with ether and dried, giving about 2.90 g of the solid barium salt of 2-(7,8-dibromohexadecyl)-glycidic acid. The salt is placed in a flask and stirred with 10 ml of 1N HCl aqueous solution. Ether is added and the mixture is stirred for 20 minutes. The ether layer is separated, washed with water and dried. On removal of the ether solvent, there is obtained 2-(7,cis-hexadecenyl)-glycidic acid as an oil.

EXAMPLE XXXI 2,2-Dimethyl-4-(1,3-dioxolane)methyl 2-tetradecyloxiranecarboxylate:

To a stirred, ice cooled solution of 3271 mg (11.5 mmole) of 2-tetradecyloxiranecarboxylic acid in 40 ml of redistilled dry tetrahydrofuran (THF) was added 1214 mg (12 mmole) of redistilled triethylamine (maintained an argon atmosphere throughout). The reaction mixture was stirred in ice for 4 hours, after which a solution of 276 mg (11.5 mmole) of dry, powdered sodium hydride in 22.0 g (0.166 mole) of 2,2-dimethyl-4-hydroxymethyl-1,3-dioxolane was added dropwise. The reaction mixture was stirred at room temperature for 41 hours. The solvent was removed on a rotary evaporator and the resulting oil was dissolved in a mixture of 50 ml of ether, 50 ml of water and 690 mg (11.5 mmole) of acetic acid. The organic layer was washed five times with water, dried over anhydrous magnesium sulfate and concentrated to dryness on a rotary evaporator to give 5.525 g of oil [GC analysis indicated 53% product]. The oil was purified by passing over a column of 454 g of silica gel (Mallincrodt CC-4) eluting with ether/hexane (1:9) followed by ether/hexane (1:4) giving the desired product [810 mg, GC analysis indicates 94.7% product]. TLC, silica gel, 2-butanone/cyclohexane (1:2), major spot R$_f$ 0.66

EXAMPLE XXXII 2,3-Dihydroxypropyl 2-tetradecyloxiranecarboxylate: To a stirred solution of 706 mg (1.77 mmole) of 2,2-dimethyl-4-(1,3 dioxolane)methyl 2-tetradecyloxiranecarboxylate in 7.36 g (70.8 mmole) of trimethyl borate was added 717 mg (11.6 mmole) of boric acid. The reaction mixture was heated on a steam bath for 20 minutes and was then concentrated to dryness on a rotary evaporator to give an oil. The oil was partitioned between ether and water. The organic layer (including some interfacial solid) was washed four times with water and once with 5% sodium sulfate (the solid gradually goes into solution). The ether layer was dried over anhydrous magnesium sulfate and concentrated to dryness on a rotary evaporator to give 575 mg of solid (90.7% crude yield). Several fractions similarly prepared were combined (944 mg) and purified by passing over a column of 70 g of silica gel (Mallincrodt CC-4) and eluting with 2-butanone/cyclohexane (2:1) to give 844 mg of solid. Recrystallization from acetone (at −40° C.) and from ether (air drying) gave 217 mg of solid, m.p. (58° C. softens) 61°-63.5° C.

EXAMPLE XXXIII

Methyl 2-(methoxycarbonyl) eicosanoate:

To a solution of 70 cc methanol was gradually added 2.4 g of sodium. When all the sodium was in solution, 15 g dimethylmalonate was added and refluxed for 5 minutes. The mixture was brought to room temperature, 33.3 g of stearyl bromide is added, refluxed for 2 hours, neutralized with HCl (1N). About two-thirds of the methanol was removed by rotavac and about 300 ml of water was added, extracted with ether, dried (MgSO$_4$) and removed, giving crude product, 23 g, 61% yield (GC). Purification by HPLC gave desired product, m.p. 51°-52° C.

EXAMPLE XXXIV

Barium 2-(methoxycarbonyl) eicosanoate:

1 g of methyl 2-(methoxycarbonyl) eicosanoate was dissolved in 200 ml methanol, 5 ml of Ba(OH)$_2$/CH$_3$OH solution added and stirred at room temperature for 3 hours. The resultant material was filtered, washed with methanol and ether and dried giving 0.92 g of barium salt.

EXAMPLE XXXV 2-(Methoxycarbonyl) eicosanoic acid:

Barium 2-(methoxycarbonyl) eicosanoate, 8 g in 80 cc 1N HCl and 240 cc ether was stirred at room temperature for 5 hours. The ether layer was separated dried over MgSO$_4$ and was removed under reduced pressure giving 5.47 g of half acid ester.

EXAMPLE XXXVI

Methyl-2-methylene eicosanoate:

To 5.36 g of the diethylamine was added slowly 13.4 ml of HCHO (37%), then to this slightly warm solution there was added 4.99 g of the 2-(methoxycarbonyl) eicosanoic acid and refluxed for an hour, then left at 60° C. overnight. The top layer separated, and the lower phase was extracted with ether. Both phases were collected, washed with 1N HCl and water and dried over MgSO$_4$. On removal of the solvent, there was obtained 3.2 g of olefin (70.3%). After dry column chromatography (silica gel) purification 1.84 g of pure olefin is obtained, m.p. 39° C.

EXAMPLE XXXVII

Methyl 2-octadecyl oxirane carboxylate:

A mixture of methyl-2-methylene eicosanoate, 2.3 g, m-chloroperbenzoic acid, 4.5 g, and 3-(t-butyl)-4-hydroxy-5-methylphenyl sulfide inhibitor in 150 cc 1,2-dichloroethane was stirred and refluxed for 5 hours, then was left overnight, precipitated and filtered. The filtrate was concentrated in vacuo to one-third of the original volume, cooled and refiltered. Ether was added to the filtrate which was then washed with K$_2$CO$_3$ solution and water. The ether layer was dried (MgSO$_4$) and evaporated to give 2.1 g of crude product. After column chromatography (dry silica gel), purification gave pure product, m.p. 58° C.

The following examples illustrate how the various antihypertensive compounds may be formulated in the form of pharmaceutical compositions having a pharmaceutically acceptable carrier present, for administration to a hypertensive animal in the method of the present invention.

EXAMPLE XXXVIII

One thousand hard gelatin capsules, each containing 200 milligrams of sodium 2-tetradecyl glycidate are prepared from the following formulation:

|  | Grams |
|---|---|
| Sodium 2-tetradecyl glycidate | 200 |
| Starch | 100 |
| Lactose | 250 |
| Talc | 50 |
| Calcium stearate | 10 |

A uniform mixture of the ingredients is prepared by blending and employed to fill two-piece hard gelatin capsules. The capsules are suitable to be orally administered to hypertensive subjects to reduce blood pressure.

EXAMPLE XXXIX

One thousand compressed tablets, each containing 500 milligrams of methyl 2-tetradecylglycidate are prepared from the following formulation:

|  | Grams |
|---|---|
| Methyl 2-tetradecylglycidate | 500 |
| Starch | 200 |
| Dibasic calcium phosphate hydrous | 200 |
| Calcium stearate | 10 |

The finely powdered ingredients are mixed well and granulated with 10% starch paste. The granulation is dried and compressed into tablets using starch as a disintegrant and calcium stearate as a lubricant.

EXAMPLE XXXX

Gelatin capsules are prepared as described in Example XXXI, except that methyl 2-tetradecylglycidate is employed as active agent.

EXAMPLE XXXXI

Compressed tablets are prepared as described in Example XXXII, except that sodium 2-tetradecylglycidate is employed as active agent.

We claim:

1. A method which comprises administering to a hypertensive animal a therapeutically-effective antihypertensive amount of a compound selected from the group consisting of glycidic and thioglycidic acid compounds having the formula:

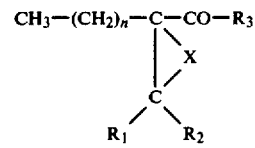

wherein n is an integer from 7 to 21; R$_3$ is a member selected from the group consisting of OH, O-loweralkyl, NH$_2$, NH-loweralkyl, and NH-loweralkyl-OH; X is a member selected from the group consisting of O and S; and each of R$_1$ and R$_2$ is a member selected from the group consisting of hydrogen and loweralkyl; or a therapeutically active basic salt of the foregoing acid.

2. A method according to claim 1 wherein said n is an integer from 7 to 19.

3. A method of reducing arterial pressure in hypertensive subjects which comprises administering to a hypertensive subject from about 1 to 500 milligrams per unit dose of a glycidic or thioglycidic acid compound having the formula:

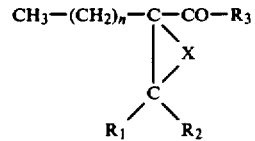

wherein n is an integer from 7 to 21; R$_3$ is a member selected from the group consisting of OH, O-loweralkyl, NH-loweralkyl, and NH-loweralkyl-OH; X is a member selected from the group consisting of O and S; and each of $R_1$ and $R_2$ is a member selected from the group consisting of hydrogen and loweralkyl; or a therapeutically active basic salt of the foregoing acid.

4. A method according to claim 3 wherein said n is an integer from 7 to 19.

5. A method according to claim 3 wherein the compound which is administered is methyl 2-tetradecylglycidate.

6. A method according to claim 3 wherein the compound which is administered is methyl 2-decylglycidate.

7. A method according to claim 3 wherein the compound which is administered is methyl 2-hexadecylglycidate.

8. A method according to claim 3 wherein the compound which is administered is methyl 2-octadecylglycidate.

9. A method according to claim 3 wherein the compound which is administered is methyl 2-tridecylglycidate.

10. A method according to claim 3 wherein the compound which is administered is methyl 2-tetradecylthioglycidate.

11. A method according to claim 3 wherein the compound which is administered is 2-tetradecylglycidic acid.

12. A method according to claim 3 wherein the compound which is administered is 2-tetradecylglycidamide.

13. A method according to claim 3 wherein the compound which is administered is methyl 2-tetradecyl-3,3-dimethylglycidate.

14. A method according to claim 3 wherein the compound which is administered is N-(2-hydroxyethyl)-2-tetradecylglycidamide.

15. A method according to claim 3 wherein the compound which is administered is 2,3-dihydroxypropyl 2-tetradecylglycidate.

16. A method according to claim 3 wherein the compound which is administered is methyl 2-(cis-7,8-hexadecenyl)-glycidate.

* * * * *